United States Patent

Wolter

[11] Patent Number: 5,451,215
[45] Date of Patent: Sep. 19, 1995

[54] SUCTION DRAIN FOR THE ASPIRATION OF DISCHARGES

[76] Inventor: Dietmar Wolter, BG Unfallkrankenhaus Bergedorfer Strasse 10, 2050 Hamburg 80, Germany

[21] Appl. No.: 372,885

[22] Filed: Jan. 13, 1995

Related U.S. Application Data

[63] Continuation of Ser. No. 86,926, Jul. 2, 1993, abandoned, which is a continuation-in-part of Ser. No. 760,733, Sep. 16, 1991, abandoned.

[30] Foreign Application Priority Data

Sep. 17, 1990 [DE] Germany ............................. 9013184

[51] Int. Cl.⁶ ............................................. A61M 11/00
[52] U.S. Cl. ...................... 604/265; 604/93; 604/264
[58] Field of Search ................ 604/93, 264, 266, 268, 604/269, 280, 265

[56] References Cited

U.S. PATENT DOCUMENTS

| 3,566,874 | 3/1971 | Sheperd et al. ............ 604/265 |
| 3,566,874 | 3/1971 | Shepard et al. . |
| 3,598,127 | 8/1971 | Wepsic ....................... 604/265 |
| 4,186,745 | 2/1980 | Lewis et al. ................. 604/265 |
| 4,603,152 | 7/1986 | Laurin et al. ............... 604/265 |
| 4,731,054 | 3/1988 | Billeter et al. .............. 604/280 |
| 4,950,415 | 10/1990 | Reinmuller ................. 604/265 |
| 4,960,415 | 10/1990 | Reinmuller . |
| 5,049,138 | 9/1991 | Chevalier et al. ........... 604/265 |

FOREIGN PATENT DOCUMENTS

| 2256769 | 8/1975 | France . |
| 3115763 | 11/1982 | Germany ................... 604/265 |
| 3533369A1 | 3/1987 | Germany . |
| 0035036 | 10/1979 | Japan ........................ 604/265 |
| WO89/05671 | 6/1989 | WIPO . |
| 8905671 | 6/1989 | WIPO . |

OTHER PUBLICATIONS

German Search Report for G 90 13 184.

Primary Examiner—C. Fred Rosenbaum
Assistant Examiner—N. Kent Gring
Attorney, Agent, or Firm—Chilton, Alix & Van Kirk

[57] ABSTRACT

A suction drain for the aspiration of fluids from a body, comprising an elongated, tubular first portion to be introduced into a body, the first portion having a generally constant outer diameter and a plurality of openings along substantially its entire length, an interior portion, an exterior surface, and a terminal end supporting an antibacterial material, wherein the antibacterial material is in the form of an end-cap which extends longitudinally outward from the terminal end of the first portion and which has an outer diameter that is no larger than the outer diameter of the first portion.

17 Claims, 2 Drawing Sheets

SUCTION DRAIN FOR THE ASPIRATION OF DISCHARGES

This is a continuation of copending application Ser. No. 08/086,926 filed on Jul. 2, 1993, now abandoned which is a continuation-in-part of application Ser. No. 07/760,733 filed on Sep. 16, 1991, now abandoned.

BACKGROUND AND SUMMARY OF THE INVENTION

The invention relates to a suction drain for the aspiration of discharges and other fluids from the human or animal body, which is provided with a material depot with an antibacterial action.

It is known that it is possible by use of suction drains, for example, Redon suction drains, to considerably reduce hematoma formation and tissue water accumulation in surgical wounds. This leads to improved wound healing because apposition of the tissue layers is possible and thus they heal directly.

In every operation there is, despite all precautions, contamination with microbes. As a rule, the body's own defenses succeed in killing the microbes which have entered the wound.

A factor favoring the development of an infection in the surgical wound is the collection of discharge. This is where the conventional Redon drain has, owing to the aspiration of discharge, a prophylactic action preventing infection. One current possibility for the therapy of infected wounds is to insert polymethacrylate beads which contain an antibiotic into the wound. Owing to the diffusion of the antibiotic, there is release of the antibiotic over the course of days, weeks and months into the surroundings and thus an effective local control of microbes. It is unnecessary to expose the whole body to antibiotics, for example by oral intake. The chains of beads have, however, the disadvantage that, as a rule, they have to be removed surgically, which means that the patient must undergo a second operation.

In the case of a suction drain of the type specified in the introduction, it is known to enclose a material depot with an antibacterial action in a semipermeable membrane, in particular a semipermeable tube, which is then connected to the suction drain, for example inserted into this suction drain. However, this results in a comparatively complicated construction of the suction drain. Moreover, in previously disclosed embodiments (German Offenlegungsschrift 35 06 288) it is unclear where, and in general how, aspiration is effected. It is apparently the case that aspiration takes place only in the immediate vicinity of the material depot with an antibacterial action so that the substances with an antibacterial action move only a very short distance through the wound. Moreover, the position of the material depot is not accurately defined because the semipermeable tube is apparently very flexible.

It is furthermore known to provide the material depot at the end of the suction tube in the interior thereof in the vicinity of one or more openings (WO89/05671). However, in this case a medicinal action occurs only in the vicinity of the opening or only in the interior of the tube, which is also the thing that is actually essential in the case of a urine catheter, because the essential need is only to avoid unwanted reactions in the interior of the catheter.

It is furthermore known to provide essential parts of the catheter with material depots with an antibacterial action (DE-A 35 33 369, US-A 3 598 127). However, in this case it is again impossible to take account of the requirement that, especially during wound drainage, a greater antibacterial action is necessary at the suction drain tube end which is to be introduced into the body, the distal end of this tube, than in regions of the tube which are located more towards the end remote from the body.

The object of the invention is to provide a suction drain of the type mentioned in the introduction, which on the one hand has a simple construction, and on the other hand is very effective.

This is achieved according to the invention by the suction drain being provided along its longitudinal extent with a plurality of openings, and the material depot terminating the suction tube end to be introduced into the body.

Thus, firstly, the suction drain has a plurality of openings along the longitudinal extent, so that the discharge can be aspirated not only at the end of the suction tube. On the other hand, the material depot terminates the end of the suction tube, that is to say it is located at the end of the tube and lies freely and is thus not, as with the previously disclosed urine catheter (WO89/05671), essentially enclosed by the end of the tube. Here the material with an antibacterial action is in direct contact with the body tissue and can easily enter the body, spread there and then be aspirated with the discharges and other fluids to the openings and through the openings. In this way a larger region of the wound is treated with agents with an antibacterial action, the action decreasing with the distance from the distal end of the tube. This results in a particularly advantageous dosage along the longitudinal extent of the tube. It is also necessary for the antibacterial material always first to move a certain distance in the wound or the like before it is then aspirated with the discharge.

However, the particular advantages apply not only to suction drains which are placed in surgical wounds. On the contrary, similar advantages also occur in all other cases where a discharge must be aspirated from the human or animal body. Examples which may be mentioned here now are chest drainage or a bladder catheter, when openings are to be located not only at the end of the tube.

In an advantageous embodiment, the material depot is arranged at the suction tube end to be introduced into the body, in the interior of the tube and there partitioned off from the remainder thereof. The material depot is thus located in an anterior chamber of the tube which is partitioned off from the remainder of the tube, for example by a plug. The material with antibacterial action is then able here to diffuse out of the openings in the tube and is aspirated by the suction tube with the discharge. In this case the material with an antibacterial action moves distances which differ in length and enters the drainage tube everywhere that the latter has openings. Thus, a very large region of the surgical wound or, for example, of the chest receives antibacterial treatment. Similar effects are obtained when the material depot surrounds, in the manner of a cap, the suction tube end to be introduced into the body. Here it is further possible to provide for the cap-like material depot to be releasably attached at the end of the suction tube, so that it remains in the body when the suction tube is removed. The antibacterial action can then take place further, even after removal of the suction tube, in which case the material depot can consist of exclusively absorbable substances.

It is expedient for the size of the openings or holes in the suction tube to decrease in the direction of suction, as is known of the so-called Ulmer drain. This has the advantage that the intensity of aspiration is everywhere the same even over greater lengths of the suction tube, so that the material with an antibacterial action is also aspirated over larger regions and thus can be effective over these larger regions.

In an another advantageous embodiment, the suction tube is additionally coated with the material with an antibacterial action.

It is expedient for the material with an antibacterial action to be enclosed in a material which can be absorbed by the body. This material is then gradually absorbed, in which case the material with an antibacterial action is also gradually released and can be effective over lengthy periods.

In a particularly advantageous embodiment, the suction tube itself consists at least partially of absorbable material in which the material with an antibacterial action is contained. This results in the following considerable advantages.

The suction tube releases the material with an antibacterial action in the entire region of the surgical wound. The point at which the suction tube emerges through the skin is normally particularly critical for microbes. Since material with an antibacterial action is likewise released here at the outside of the tube, infection at this point is likewise suppressed. Another possibility is normally that microbes migrate back through the discharge into the body against the direction of suction. This is likewise prevented because the suction tube releases material with an antibacterial action everywhere, so that the microbes are unable to migrate back into the surgical wound or the other part of the body in which the suction tube is placed.

It is expedient for the material with an antibacterial action to be an antibiotic, and gentamicin is particularly expedient.

The absorbable material can be collagen, polyglycolide-lactide or another suitable polymer.

In particular, the material depot with an antibacterial action can have gentamicin or a similar antibiotic and polymethyl-methacrylate or a similar carrier substance. It is possible here to control, by different ratios of amounts, the rate at which the antibiotic is released. This rate can also be controlled by incorporating into the material different amounts of an additive which speeds up or slows down the breakdown of the material depot and thus the release of the antibiotic. The rate of release can also be controlled by the material depot being pressed with varying intensity or, for example, being constructed in the form of foam.

When the tube is composed with absorbable material it can have an intended breaking point so that a part of the tube can remain in the body when the aspiration is complete, in order to have a microbicidal action here until absorption is complete.

It would also be possible for the tube to be a vessel catheter which is used not only for aspiration but also for infusion.

The invention is described hereinafter by means of advantageous embodiments with reference to the attached drawings.

DETAILED DESCRIPTION OF THE INVENTION

Figure 1:
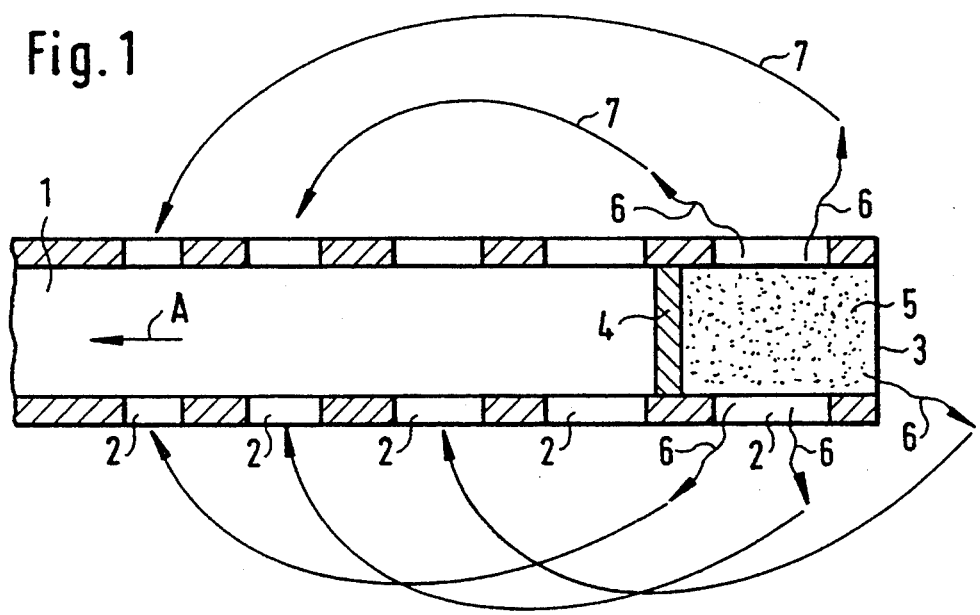
FIG. 1 shows a longitudinal section of a first embodiment of a suction tube which can be used for the suction drain of the invention.

FIG. 1 shows a cross-section of a suction tube 1 which is provided with openings or holes 2 through which the discharge can be aspirated. The suction tube i is attached to a source of reduced pressure so that the discharge is aspirated in the direction of arrow A. The diameter of the openings moreover decreases in the direction of suction, as is indicated in the figure. A so-called Ulmer drain of this type results in the suction effect being approximately the same everywhere. The tube 1 is partitioned off, near its end 3 located in the body, by a plug 4 which is, for example welded on. The material depot 5 which contains the material with an antibacterial action, for example an antibiotic such as gentamicin, is located between the plug 4 and the end 3. The antibiotic preferably is carried by polymethylmethacrylate or a similar carrier substance. The antibiotic can be embedded in material which can be absorbed by the body, such as collagen, polyglycolide-lactide or another suitable polymer. The use of a carrier material provides that the material depot 5 retains its shape even after some of the antibacterial material has been transferred into the body tissue. The material with an antibacterial action now leaves by diffusion the tube 1 through lateral openings 2 and through the front opening at the end 3, as is indicated at 6, and moves lengthy distances 7 through the wound or other body cavity until it is sucked in through the openings 2. Thus, in contrast to the state of the art, the antibacterial material acts over a greater extent of the drain tube.

Figure 2:
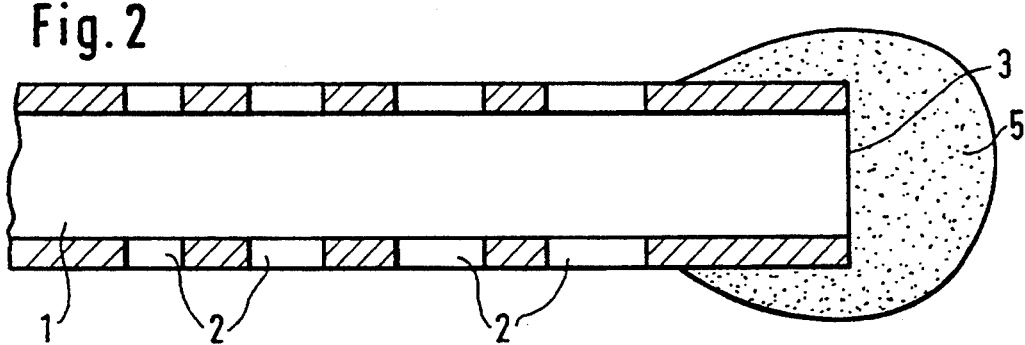
FIG. 2 shows a second embodiment.

In the embodiment in FIG. 2 the antibacterial material 5 is designed as a cap which is placed on the end 3 of the tube 1. The distances 6, 7 of the material with an antibacterial action are similar to those in FIG. 1 so that renewed representation of these distances is dispensed with. However, it is again essential that the material migrates to all suction openings 2 and thus acts in larger regions of the body cavity or wound. The cap 5 can also be placed only loosely on the drain tube 1 so that it remains in the wound after removal of the drain tube 1. In this case it ought expediently to consist completely of material which can be absorbed by the body. This embodiment can be used when the cap 5 comprises an antibacterial material which is embedded in a material which can be absorbed by the body, such as collagen, as long as the suction drain is to be kept in the body long enough that the portion of the cap of antibacterial material which extends outward to a greater diameter than the tube has been absorbed by the body. This embodiment is not recommended for use with polymethyl methacrylate, which cannot be absorbed by the body, or for short term use with an absorbable carrier, i.e., for a time which is not long enough to provide for a reduction in the diameter of the cap piece down to the diameter of the tube, because the removal of a drain with a thickened portion at the terminal end thereof might result in pain or injury to the patient.

Figure 3:
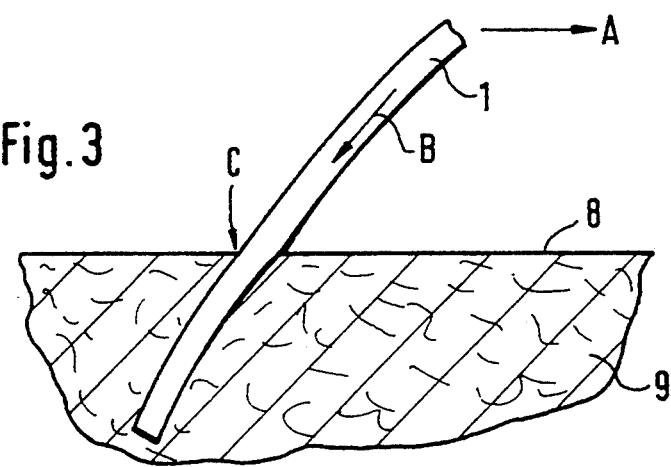
FIG. 3 shows a third embodiment.

In the embodiment of FIG. 3 the complete drain tube 1 consists of an absorbable material which contains the material with antibacterial action. If aspiration takes place here in the direction of arrow A, it is still generally not possible to prevent microbes moving in the opposite direction, namely in direction B. However, if the entire tube consists of absorbable material with an antibacterial action, material with an antibacterial action is released everywhere on the tube walls so that the microbes are killed.

This microbicidal action also exists at point C where the tube 1 enters the tissue 9 through the skin 8. This effectively prevents infection at point C. The material of the tube 1 is, of course, also absorbed in the interior of the body, and thus the material with an antibacterial action is released, so that the region of the wound or other body cavity undergoes antibacterial treatment.

Figure 4:
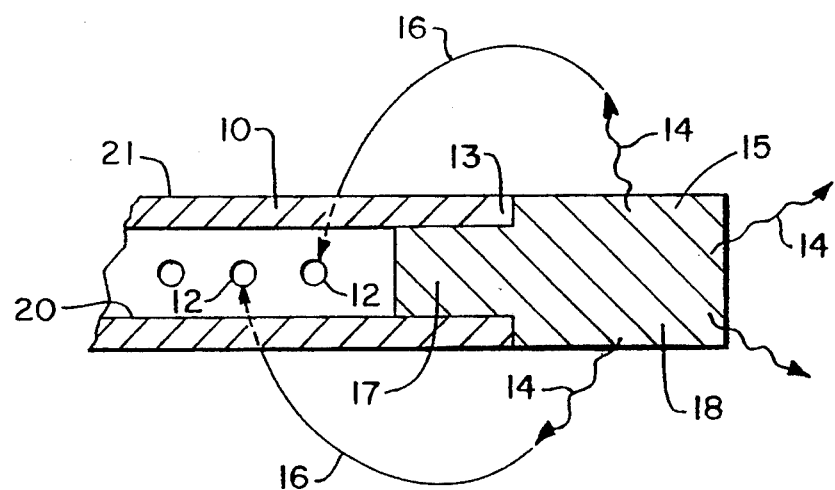
FIG. 4 shows a fourth embodiment.

FIG. 4 shows a cross-section of a tube 10 in which the antibacterial material is in the form of a cylindrical material depot or end-cap 15 which extends longitudinally outward from the end 13 of the tube 10 which is to be inserted into the body. The end-cap 15 has a first cylindrical portion 17 which has approximately the same diameter as the inner diameter 20 of the tube 10 and is received in the tube 10, and a second cylindrical portion 18 which remains outside the end 13 of the tube, is connected to the first cylindrical portion, and has a diameter which corresponds to the outer diameter of the tube 10. This configuration provides that the suction drain has a uniform outer diameter, thereby enabling the tube 10 with end-cap 15 to be removed from the body without problems.

The end-cap 15 comprises polymerized methyl methacrylate containing the active substance. To mount the first portion 17 of the end-cap 15 in the tube 10 in a preferred manner, the first portion 17 is coated with unpolymerized methyl methacrylate by dipping or other suitable means and is then pushed into the end 13 of the tube 10. The unpolymerized methyl methacrylate quickly polymerizes, thus achieving a very firm and reliable connection between the tube 10 and the end-cap 15 using a relatively uncomplicated procedure. It is believed that rapid polymerization may result from the contact of the unpolymerized methyl methacrylate with polymerized methyl methacrylate. This embodiment of the invention provides that a particularly large portion of the antibacterial material is in direct contact with the body tissue, thereby facilitating the entry of the antibacterial material into the body. As in the other embodiments of the invention, the antibacterial material moves through the tissue as indicated at 14, and moves lengthy distances 16 through the body tissue until it is removed by suction through openings 12 which extend along opposite sides of the tube 10.

What is claimed is:

1. A suction drain for the aspiration of fluids from a body, comprising an elongated, tubular first portion to be introduced into a body, the first portion having a generally constant outer diameter and a plurality of openings along substantially its entire length, an interior portion, an exterior surface, and a terminal end supporting an antibacterial material, wherein the antibacterial material is in the form of an end-cap which extends longitudinally outward from the terminal end of the first portion and which has an outer diameter that is no larger than the outer diameter of the first portion.

2. A suction drain as claimed in claim 1, wherein the antibacterial material is releasably attached to the terminal end of the first portion.

3. A suction drain as claimed in claim 1, wherein the size of the openings in the suction drain decreases in the direction of suction.

4. A suction drain as claimed in claim 1, wherein the antibacterial material is enclosed in an absorbable material which can be absorbed by the body.

5. A suction drain as claimed in claim 4, wherein the absorbable material is polyglycolidelactide.

6. A suction drain as claimed in claim 4, wherein the absorbable material is collagen.

7. A suction drain as claimed in claim 4, wherein the suction drain has an intended breaking point.

8. A suction drain as claimed in claim 1, wherein the antibacterial material is an antibiotic.

9. A suction drain as claimed in claim 1, wherein the antibacterial material is gentamicin.

10. A suction drain as claimed in claim 1, wherein the antibacterial material has gentamicin as an antibiotic and polymethyl-methacrylate as a carrier substance.

11. A suction drain as claimed in claim 1, wherein the antibacterial material includes an antibiotic in a carrier, and the rate of release of the antibiotic depends upon the ratio of the antibiotic and the carrier.

12. A suction drain according to claim 1, wherein the end-cap has a first cylindrical portion which is configured to be positioned within the first portion at the terminal end and a second cylindrical portion which is connected to the first cylindrical portion and is configured to be positioned outside the first portion.

13. A suction drain according to claim 1, wherein the end-cap is configured to permit diffusion of antibacterial material into the body in a flow direction which is generally parallel to the length of the tube.

14. A suction drain for the aspiration of fluid from a body, comprising:
a suction tube having a length and an elongated first portion with a generally constant outer diameter to be introduced into the body, the first portion having a plurality of openings along substantially the entire length thereof for discharge of the fluid, and a terminal end having an antibacterial material positioned thereon, the antibacterial material being in the form of an end-cap which extends longitudinally outward from the terminal end of the first portion away from the first portion, has a diameter that is no larger than the outer diameter of the first portion, and contains polymethyl methacrylate as a carrier.

15. A suction drain according to claim 14, wherein the antibacterial material is releasably attached to the terminal end of the first portion.

16. A method of making a suction drain, comprising:
obtaining an elongated, narrow tube to be introduced into a body, the tube including a length and a first portion having a generally constant outer diameter, the first portion having a plurality of openings along substantially its entire length and a terminal end, and adhering an end-cap comprising antibacterial material to the terminal end of the first portion, the end-cap extending longitudinally outward from the tube and having a diameter which is no larger than the diameter of the first portion of the tube, the end-cap being positioned to permit diffusion of antibacterial material into the body in a flow direction which is generally parallel to the length of the tube.

17. A method according to claim 16, wherein the end-cap contains polymethyl methacrylate and the end-cap is adhered to the terminal end of the tube using methyl methacrylate.

* * * * *